(12) United States Patent
Johannaber

(10) Patent No.: US 9,629,642 B2
(45) Date of Patent: Apr. 25, 2017

(54) HIP RESURFACING DRILL GUIDE DEVICE

(71) Applicant: SYNVASIVE TECHNOLOGY, INC., El Dorado Hills, CA (US)

(72) Inventor: Kenneth Dale Johannaber, Reno, NV (US)

(73) Assignee: SYNVASIVE TECHNOLOGY, INC., El Dorado Hills, CA (US)

( * ) Notice: Subject to any disclaimer, the term of this patent is extended or adjusted under 35 U.S.C. 154(b) by 397 days.

(21) Appl. No.: 14/224,920

(22) Filed: Mar. 25, 2014

(65) Prior Publication Data

US 2015/0272597 A1    Oct. 1, 2015

(51) Int. Cl.
*A61B 17/17*  (2006.01)
*A61B 17/56*  (2006.01)
*A61B 90/00*  (2016.01)

(52) U.S. Cl.
CPC .......... *A61B 17/1721* (2013.01); *A61B 17/17* (2013.01); *A61B 17/175* (2013.01); *A61B 17/1739* (2013.01); *A61B 17/1742* (2013.01); *A61B 17/56* (2013.01); *A61B 2017/564* (2013.01); *A61B 2090/036* (2016.02); *A61B 2090/0811* (2016.02)

(58) Field of Classification Search
CPC . A61B 17/17; A61B 17/1721; A61B 17/1739; A61B 17/1742; A61B 17/175; A61B 17/56; A61B 2017/564
See application file for complete search history.

(56) References Cited

U.S. PATENT DOCUMENTS

| | | | |
|---|---|---|---|
| 2004/0146830 A1 | 7/2004 | Weinstein | |
| 2005/0113841 A1* | 5/2005 | Sheldon | A61B 17/1668 606/88 |
| 2007/0233136 A1* | 10/2007 | Wozencroft | A61B 17/175 606/86 R |
| 2008/0033442 A1 | 2/2008 | Amiot | |

(Continued)

OTHER PUBLICATIONS

Biomet UK, Ltd., Recap (R) KS Design Rationale, Surgical Technique and Design Rationale, 2007, Form No. B010027.0, REV121507, Warsaw, Indiana, United States of America.

(Continued)

*Primary Examiner* — Larry E Waggle, Jr.
(74) *Attorney, Agent, or Firm* — Norton Rose Fulbright Canada LLP

(57) ABSTRACT

A device for guiding a drilling of a femoral head of a femur in femoral head resurfacing comprises a body defining a guide channel adapted to receive and guide a drilling component therein. Arms are pivotally connected to the body and biased toward one another, the arms each having a contact end extending below the body, the contact ends adapted to contact a femoral neck when the body is in a hovering position relative to the femoral head. Sensors produce a signal indicative of an orientation angle of each of the arms relative to the body. A processor unit calculates the orientation angles of the arms from the signal, and evaluates from the orientation angles an alignment of the body relative to the femur. A visual output produces a visual signal representative of said alignment. A method for aligning a drill guide device on a femur for subsequent drilling a femoral head with a guide channel in the drill guide device is also provided.

26 Claims, 7 Drawing Sheets

(56) References Cited

U.S. PATENT DOCUMENTS

| | | | | |
|---|---|---|---|---|
| 2009/0254093 A1* | 10/2009 | White | ............... | A61B 17/175 |
| | | | | 606/89 |
| 2010/0030116 A1* | 2/2010 | Chana | ................. | A61B 5/103 |
| | | | | 600/587 |
| 2010/0292743 A1* | 11/2010 | Singhal | ............. | A61B 17/175 |
| | | | | 606/86 R |
| 2011/0077650 A1* | 3/2011 | Braun | ............... | A61B 17/175 |
| | | | | 606/56 |
| 2012/0323247 A1 | 12/2012 | Bettenga | | |

OTHER PUBLICATIONS

Biomet UK, Ltd., ReCap Femoral Resurfacing System, Surgical Technique, Jan. 2005, 01-50-0930, Form No. Y-BMT-928/101505/M.

\* cited by examiner

HIP RESURFACING DRILL GUIDE DEVICE

TECHNICAL FIELD

The present application relates to hip resurfacing in computer-assisted surgery.

BACKGROUND OF THE ART

Hip resurfacing consists in the implanting of a femoral head implant on a resurfaced femoral head, and the resurfacing of the acetabulum for the insertion therein of a cup implant. In such cases, the surgeon judges that the femoral neck is strong enough to remain unaltered, and the femoral head implant is used to replace damaged femoral head bone material. In comparison with total hip joint implanting surgery, the hip joint resurfacing surgery removes a relatively small amount of femoral bone while providing high levels of joint stability.

Different output values are of concern in hip replacement surgery. In order to reproduce a natural and/or improved gait and range of motion to a patient, the position and orientation of the implants, the offset of the femur and the limb length must be considered during surgery. The work of the surgeon during hip replacement surgery will have a direct effect on these output values.

Known hip joint resurfacing surgery techniques presently involve specific tools so as to obtain precise position and orientation for the implants. As various types of reamers are used to resurface the femoral head, alignment steps are performed to align the tools with the cuts to be made. It is, for instance, of nonnegligible importance that the femoral neck not be damaged (i.e., notched) by the reamers, to prevent fracture-prone weakness in the femoral head. Moreover, the resurfacing must be as precise as possible, for instance, to reduce the amount of cement required for implanting the ball head implant to the resurfaced ball head.

Hence, the positioning of the femoral component is vital to the success of hip resurfacing. However, due to the limited exposure of the femoral head in minimally invasive surgery, femoral-axis alignment may be difficult to visualize intraoperatively. Accordingly, radiographic instrumentation, such as a C-arm, is often required, and this adds costs and time to the procedure.

SUMMARY

It is an aim of the present disclosure to provide a hip resurfacing drill guide device that addresses issues related to the prior art.

Therefore, in accordance with the present disclosure, there is provided a device for guiding a drilling of a femoral head of a femur in femoral head resurfacing comprising: a body, the body defining at least one guide channel adapted to receive and guide a drilling component therein; arms pivotally connected to the body and biased toward one another, the arms each having a contact end extending below the body, the contact ends adapted to contact a femoral neck when the body is in a hovering position relative to the femoral head; at least one sensor producing a signal indicative of an orientation angle of each of the arms relative to the body; a processor unit for calculating the orientation angles of the arms from the signal, and for evaluating from the orientation angles an alignment of the body relative to the femur; and a visual output producing a visual signal representative of said alignment.

Further in accordance with the present disclosure, there is provided A method for aligning a drill guide device on a femur for subsequent drilling a femoral head with a guide channel in the drill guide device, comprising: positioning a body of the guide device in a hovering position above a femoral head by passing arms of the guide device over the femoral head to a biased grasping engagement with the femoral neck; and displacing the body in the hovering position until each of the arms is at a desired orientation angle relative to the body of the guide device, based on an output provided by the guide device.

DETAILED DESCRIPTION

Figure 1:
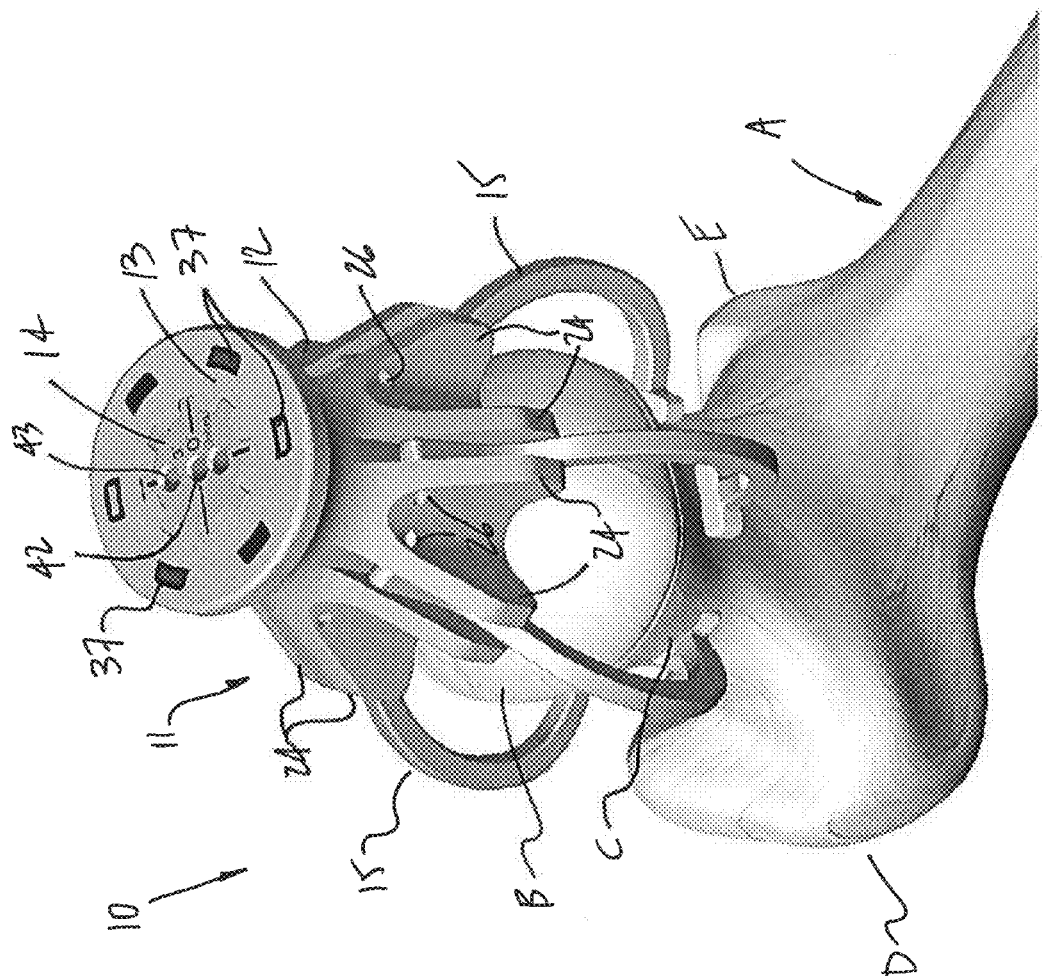
FIG. 1 is a perspective view of a hip resurfacing drill guide device in accordance with the present disclosure, as installed on the femur for subsequent use.

Referring to the drawings, and more particularly to FIG. 1, there is illustrated a hip resurfacing drill guide device 10 relative to the femur A. The femur A is shown prior to resurfacing, and has a femoral head B, a femoral neck C, a greater trochanter D and a lesser trochanter E, among other parts. The hip resurfacing drill guide device 10 is used to position a guide wire or pin into the femoral head, or to drill a guide hole in the femoral head B with a drill bit. The guide wire is then used as a guide for a cylindrical reamer, a cannulated drill or like resurfacing tool, used to remove bone from the femoral head, and hence shape same for subsequent positioning of a ball head implant on the resurfaced femoral head. The hip resurfacing drill guide device 10 is used to guide an operator in precisely and accurately positioning the guide wire in the femoral head B, which guide hole may extend into the femoral neck C as well. For simplicity, the device 10 will be referred to hereinafter as guiding the drilling of the femoral head B, which expression includes positioning a guide wire and/or drilling a hole in the femoral head B.

Figure 2:
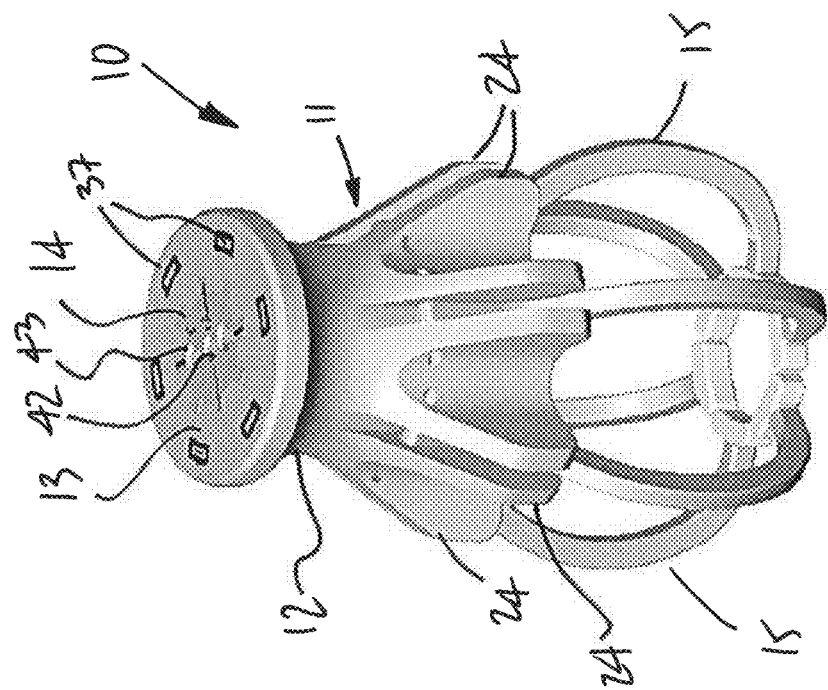
FIG. 2 is a perspective view of the hip resurfacing drill guide device of FIG. 1.
Figure 3:
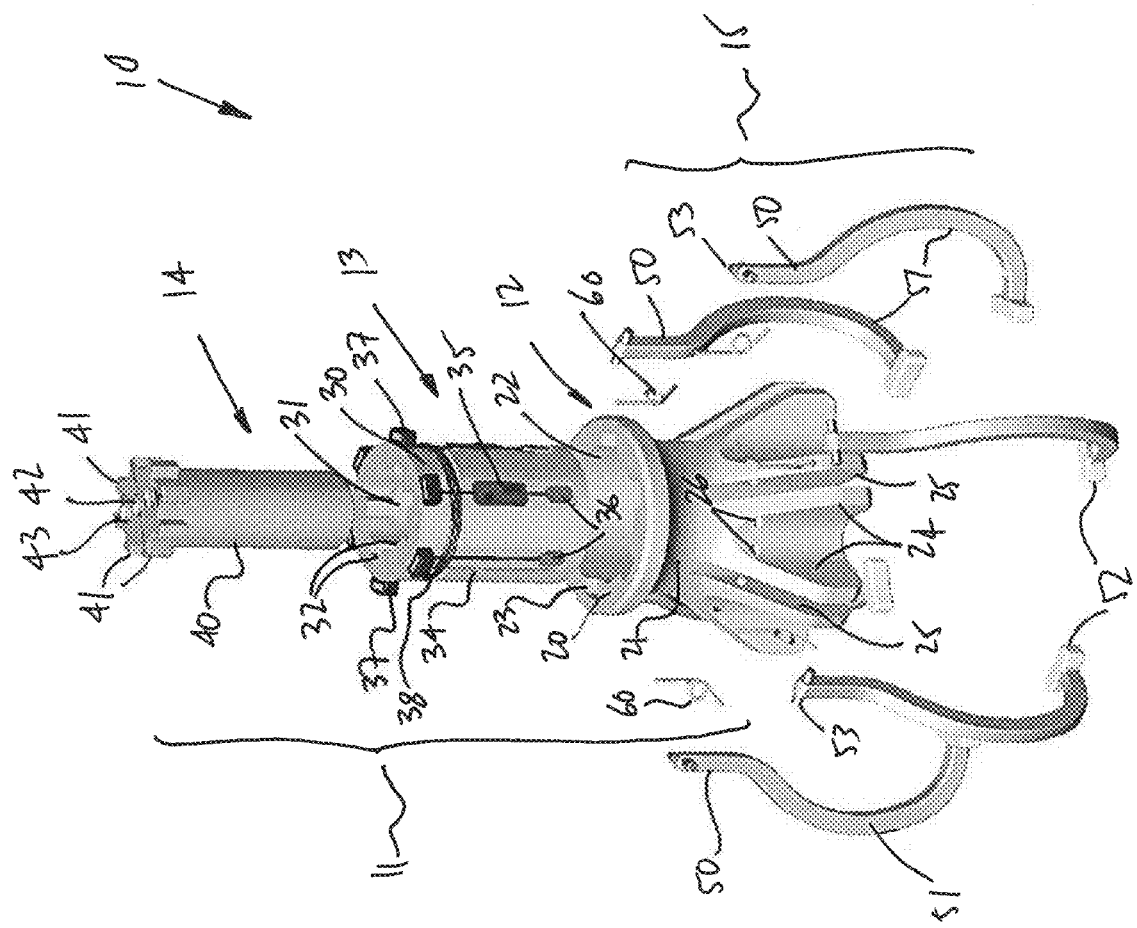
FIG. 3 is an exploded view of the hip resurfacing drill guide device of FIG. 1.

Referring to FIGS. 2 and 3, the hip resurfacing drill guide device 10, referred to hereinafter as device 10 for simplicity, is shown having a body 11 consisting of an outer shell 12, an inner body housing 13, and an adjustable pin shaft 14. Contact arms 15 are pivotally connected to the body 11.

The outer shell 12 constitutes the main structural component of the device 10, to which are directly or indirectly connected the other components.

The inner body housing 13 is a cartridge-like unit that is inserted in the outer shell 12 and supports the electronic components allowing computer-assisted surgery to be performed with the device 10. It is pointed out that the inner body housing 13 may be an integral part of the outer shell 12, as opposed to being removable therefrom as shown in FIG. 3.

The adjustable pin shaft 14 defines the guide channel(s) in which a guide wire or drill bit is inserted and drilled into the femoral head B.

The contact arms 15 are the main interface between the device 10 and the femoral neck C. The contact arms 15 are configured to allow the hovering position of the body 11 above to the femoral head B, as shown in FIG. 1. The contact arms 15 are typically provided in pairs, such as four, six, eight pairs of contact arms 15.

Still referring to FIGS. 2 and 3, the outer shell 12 is shown having a cylindrical receptacle 20. The cylindrical receptacle 20 has an annular wall 21 defining an inner cavity 22. The inner cavity 22 is sized to receive therein the inner body housing 13, whereby the inner cavity 22 is sized for the precise fit of the inner body housing 13 therein. Although not visible, the cylindrical receptacle 20 may have an opened bottom end or closed bottom end, provided that there are openings therein for the guide wire to pass therethrough. Seats 23 are circumferentially and equidistantly distributed at a top edge of the cylindrical receptacle 20, in spline-like fashion. It is observed that the number of seats 23 corresponds to the number of contact arms 15 in this illustrated embodiment. On an outer surface of the wall 21, wings 24 project radially. The wings 24 are paired with one another to define grooves 25 therebetween. As observed in FIG. 3, the grooves 25 are defined by a pair of parallel surfaces defined by the wings 24, and will receive therein ends of the contact arms 15 as described hereinafter. Pivot bores 26 are adjacent to an upper end of the wings 24, and will received pivots for the contact arms 15, as described hereinafter.

The outer shell 12 is made of any appropriate material (e.g., plastics, metals, etc). For instance, the outer shell 12 is made of a reusable material that may be autoclaved, while the inner body housing 13 may be replaceable. Alternatively, the device 10 may be a one-time use device.

Still referring to FIG. 3, the inner body housing 13 has a tubular wall 30. As mentioned previously, although the inner body housing 13 is shown a withdrawn position relative to the outer shell 12, these two components may be integrally connected, or secured to one another by way of a fastener to block such withdrawal movement. The tubular wall 30 defines an inner cavity 31 in which the adjustable pin shaft 14 will be received, whereby the inner cavity 31 is sized for the precise fit of the adjustable pin shaft 14 therein. A plurality of seats 32 are also provided in the inner cavity 31 adjacent to an upper end of the inner body housing 13. The seats 32 are arranged in a spline-like arrangement, similarly to the seats 23 of the cylindrical receptacle 20.

Longitudinal and annular slots 34 may be formed in an outer surface of the tubular wall 30. The slots 34 correspond to the number of seats 23 and hence to the number of contact arms 15. The slots 34 are shown as accommodating a printed circuit board 35 (PCB), as well as sensors 36 and LED units 37. As shown hereinafter with reference to FIG. 7, the PCB 35 incorporates a processing unit that may be programmed to operate a flow of procedures in accordance with the use of the device 10. Moreover, the PCB 35 may be programmed to operate specific functions related to a patient in particular. The sensors 36 may be Hall-effect sensors, linear potentiometers or the like that are each configured to measure an orientation of an associated contact arm 15 relative to the body 11. In the illustrate embodiment, each of the sensors 36 is paired with one of the LED units 37. The LED units 37 are arranged in spline-like fashion, and project radially from a top portion of the inner body housing 13. When the inner body housing 13 is received in the outer shell 12 in the manner shown in FIG. 2, the LED units 37 will each be received in one of the seats 23 of the cylindrical receptacle 20, whereby the inner body housing 13 is firmly connected to the outer shell 12, to block movements of one relative to another. Accordingly, a top surface of the device 10 is generally planar and continuous. It is observed that the LED units 37 are each aligned with a respective contact arm 15, with each of the LED units 37 providing an output related to the orientation of its respective contact arm 15. The LED units 37 are one of numerous possible visual indicators that may be used, and may for instance be capable of producing dual outputs, such as green and red lights. Wiring 38 interconnects the PCB 35, the sensors 36 and the LED units 37, with the wiring 38 received in the slots 34.

Figure 4:
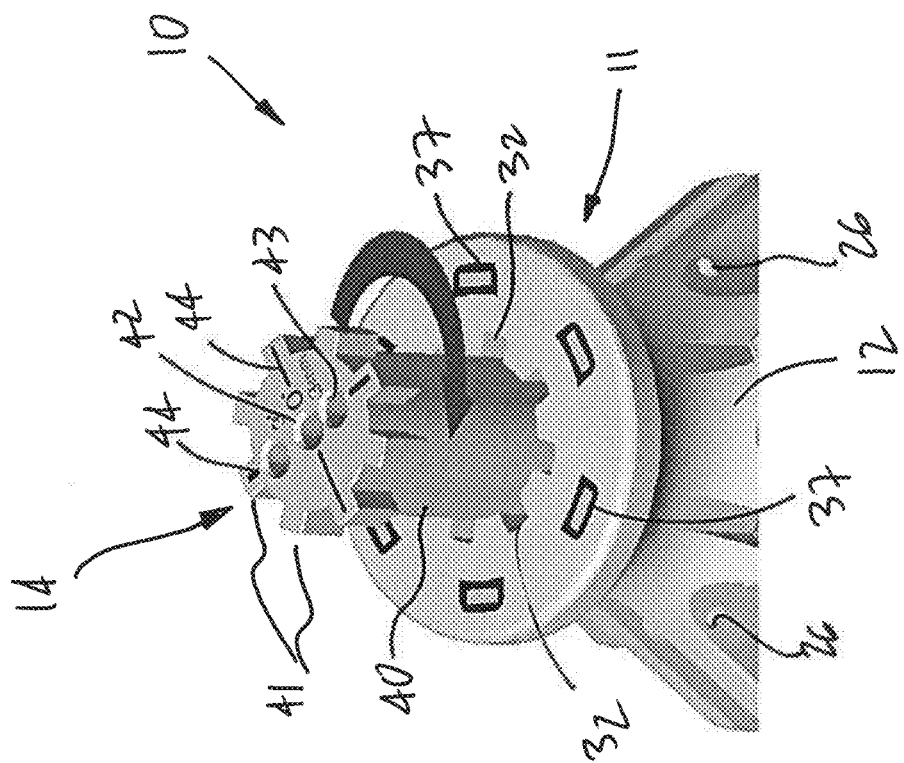
FIG. 4 is an enlarged view of an adjustable pin shaft of the hip resurfacing drill guide device of FIG. 1.

Referring to FIGS. 3 and 4, the adjustable pin shaft 14 is shown having an elongated cylindrical core 40. Spline-like portions 41 project radially from the elongated cylindrical core 40, and are in a number equivalent to that of the seats 32 in the tubular wall 30. Accordingly, when the adjustable pin shaft 14 is received in the inner cavity 31 of the inner body housing 13, the spline-like portions 41 are received in the seats 32 to reach the arrangement of FIG. 2, in which the adjustable pin shaft 14 is firmly connected to the inner body housing 13, to block movements of one relative to another, although an axial movement of the adjustable pin shaft 14 in and out of the inner cavity 31 may be possible when desired: as shown in FIG. 4, it is possible to remove the adjustable pin shaft 14 from engagement in the inner cavity 31 to adjust an orientation of the elongated cylindrical core 40 relative to that of the tubular wall 30, with ten different possible orientations (i.e., ten seats 32 are illustrated) although fewer or more of these seats 32 could be present). Other complementary engagement means are possible as well to adjust an orientation of the pin shaft 14 relative to the outer shell 12.

The elongated cylindrical core 40 is further shown as having a central guide channel 42. The central guide channel 42 is concentric with a remainder of the body 11. Alternatively, or supplementally, secondary guide channel(s) 43 may be provided as well. Both guide channels 42 and 43 project through the elongated cylindrical core 40, and through the whole body 11, such that a guide wire or drill bit inserted through a top end of the device 10 may then drill into the femoral head B, along direction lines shown in FIG. 6. The central channel 42 allows a concentric guidance as shown as X. The secondary channels 43 may provide different guiding approaches to drilling. For instance, the secondary guide channel 43 identified in FIG. 4 as being 3 degrees may be used to drill a hole in the femoral head B that is offset by an offset angle of 3 degrees relative to the concentric guide direction X, as shown by guide direction X1 in FIG. 6, the angle α being of 3 degrees. Likewise, the secondary guide channel 43 shown as labelled as 3 mm, allows a parallel offset drill bore as shown by X2 in FIG. 6, by an offset distance of 3 mm from the concentric guide direction X (concentric with the longitudinal axis of the body 11). Other offset angles and offset distances may be used as well. The top surface of the elongated cylindrical core 40 also show marker lines 44, which provide a visual indication for alignment of the adjustable pin shaft 14 relative to the outer shell 12. Considering that the channels 42 or 43 are used as a guide for a guide wire or drill bit, the material of the channels 42 or 43 must be capable of being unaltered by the drilling motion. Among numerous examples, some metals may be used, whether it be as a sleeve in the core 40. Alternatively, the core 40 may be a monolithic piece (e.g., metallic material). The diameter of the channels 42 or 43 is selected as a function of the standard guide wires, or based on a desired guide wire size specific to the patient.

As shown in FIGS. 2, 3 and 5A-5B, each of the contact arms 15 may have a straight portion 50 by which the contact arms 15 are pivotally connected to the body 11. There follows a downward curved portion 51 and end contact pads 52 at a free end of the contact arms 15. The straight portions 50 are connected by way of pivots 53 to the outer shell 12, with the pivots 53 received in the pivot bores 26. The grooves 25 defined by the wings 24 in the outer shell 12 constraint movement of the contact arms 15 relative to the outer shell 12 to the pivoting movements about the respective pivot 53 (i.e., a single rotational degree of freedom, and no translations, relative to the body 11). The curved portions 51 are sized so as not to come in contact with the femoral head B as shown in FIG. 6, while the contact arms 15 are long enough for the contact pads 52 to come into contact with the femoral neck C. Stated differently, when the body 11 hovers over the femoral head B, the curved portions 51 ensure that there is no contact of the contact arms 15 with the femoral head B. The contact pads 52 may have a curved shape to ensure suitable contact with the natural curvature of the femoral neck C. The contact pads 52 may feature a relatively rigid resilient material contacting the femoral neck C.

As shown in FIG. 3, springs 60 may be provided to bias the contact arms 15 toward a common center, in the manner illustrated in FIG. 2. The springs 60 may be torsion springs although other biasing members may also be used (e.g., coil springs, tendons, etc). Accordingly, the contact arms 15 will be urged toward one another, so as to grasp the femoral neck C in the manner depicted by FIG. 1, with the body 11 hovering above the femoral head B, for drilling the femoral head B with the guide wire inserted in the guide channel 42 or 43. The springs 60 provide sufficient biasing force for the contact arms 15 to preserve the hovering position of the body 11 in spite of the drilling action with the guide wire in the channel 42 or 43.

Figure 5B:
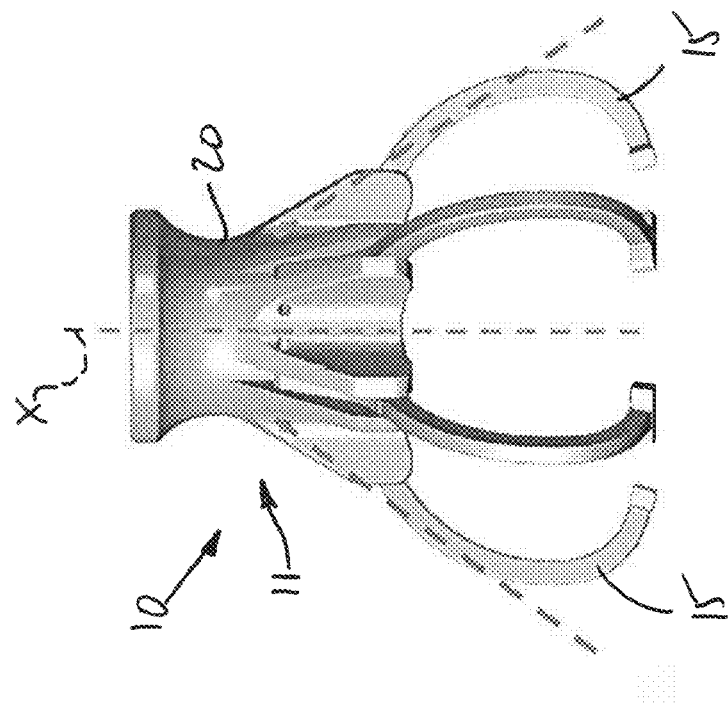
FIG. 5A and FIG. 5B are elevation views showing a "no drill" condition and a "drill" condition, respectively.
Figure 5A:
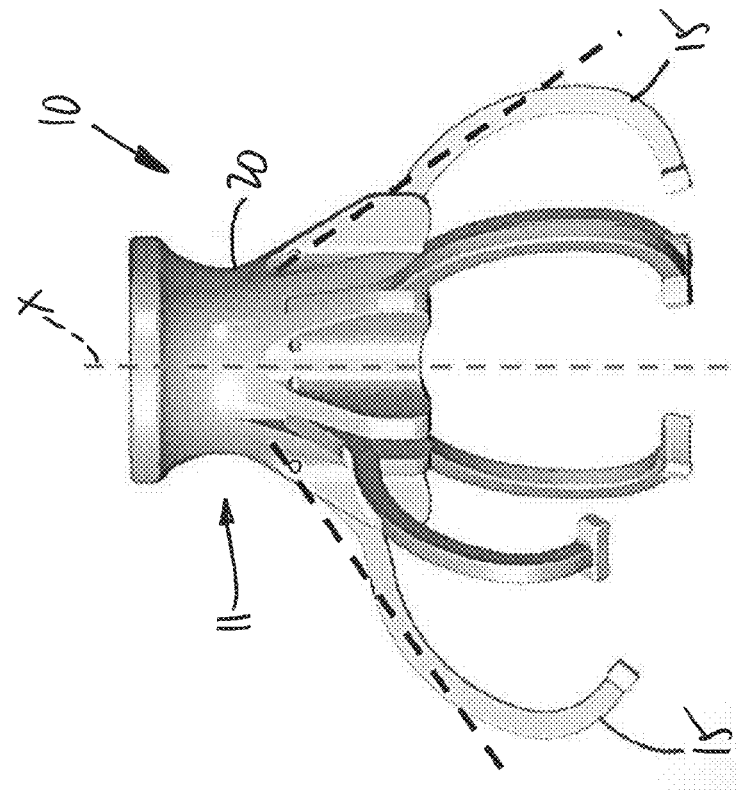
Figure 6:
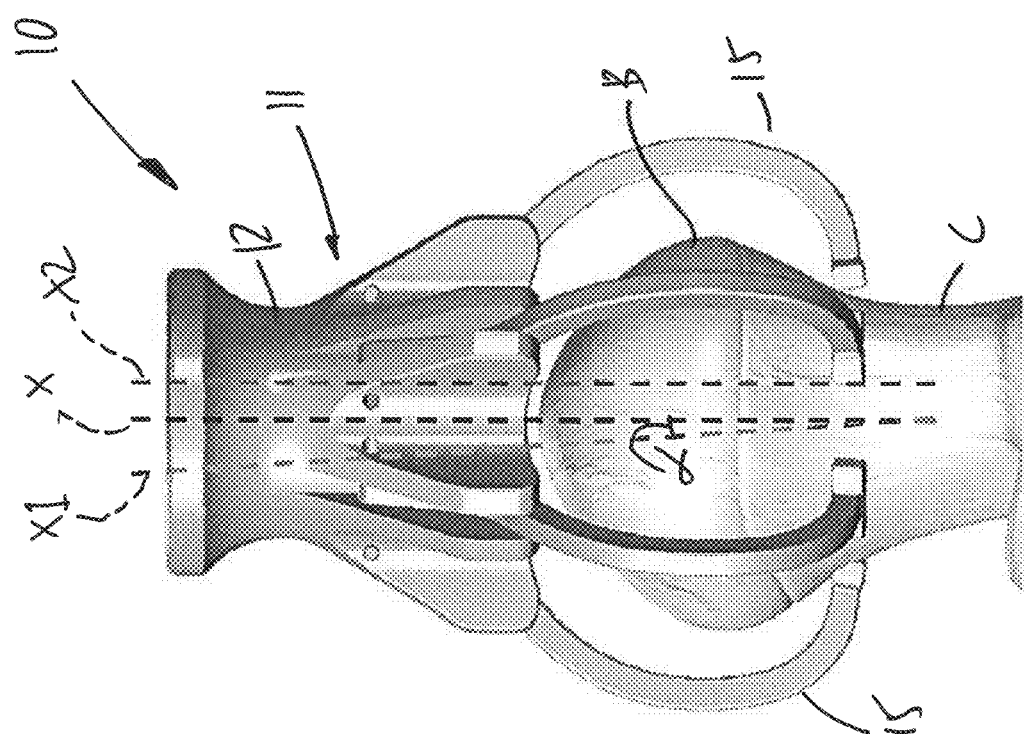
FIG. 6 is an elevation view of the hip resurfacing drill guide device in a "drill" condition relative to the femur, showing contemplated drill lines.

Referring to FIGS. 5A and 5B, the hip resurfacing drill guide device 10 is configured to indicate when the contact arms 15 are each at desired angle (i.e., a desired orientation) relative to the body 11, which desired angle may be preprogrammed in the processor of the device 10. According to an embodiment of a program, it is desired that diametrically opposed pairs of contact arms 15 be at a same angle relative to the body 11. In such an embodiment, FIG. 5A shows that two diametrically opposed contact arms 15 are oriented at a different angle relative to the body 11. In such a condition, referred to as a "no drill condition", the processor will indicate that the device 10 is improperly positioned relative to the femur. More specifically, in the illustrated embodiment, LED units 37 (FIG. 2) associated with the contact arms 15 (i.e., adjacent thereto) will light up in red to indicate that the contact arms 15 are not evenly spaced—the angles being different. Alternatively, if pairs of diametrically opposed contact arms 15 are at a same orientation relative to the body 11, the LED units 37 may lit up in green. For instance, FIG. 5B shows a "drill condition" in which pairs of diametrically opposed contact arms 15 are angled to the same degree. In the program described above, comparing diametrically opposed pairs, a single LED unit 37 could be used for each pair, although individual LED units 37 for each contact arm 15 is possible as well.

As the various components of the device 10 have been described, a use thereof is now set forth.

When the femoral head B is accessible intraoperatively, and necessary preparation has been done (e.g., removal of soft tissue, osteophytes, etc), the device 10 is positioning to the hovering position of FIG. 1, with the contact arms 15 against the femoral neck C. Accordingly, when the hip resurfacing drill guide device 10 is positioned on the femur A in the manner shown in FIG. 1, the contact arms 15 may pivot away until the position of FIG. 1 is reached, against the biasing forces produced by the springs 60.

Once the hovering position is reached (with the body 11 contacting or not the femoral head B), the operator may then move the body 11 around in rotation and translation to a visually aligned position. The LED units 37 will output a signal indicative of the alignment, e.g., whether the body 11 is a "drill" or "no drill condition", in accordance with the program selected for the patient. The operator will thus continue moving the body 11 until a drill condition is reached, guided in displacing the body 11 by the LED units 37 that indicate a proper orientation of the contact arms 15 and those showing an improper orientation of the contact arms 15. This is possible by the biasing action of the contact arms 15 that are biased into contact with the femoral neck C. Once a drill condition as per the output of the LED units 37, it may be desired that the pin shaft 14 be visually aligned with landmarks on the femur A (such as the trochanters D or E, etc). For this purpose, the operator uses the marker 44 to adjust an orientation of the adjustable pin shaft 14 in the manner shown in FIG. 4, by pulling the adjustable pin shaft 14 out of engagement with the body 11. Once the pin shaft 14 is aligned, a drill bit/guide wire/pin may be used with any one of the channels 42 and 43 to perform a drilling operation in the femoral head B.

Figure 7:
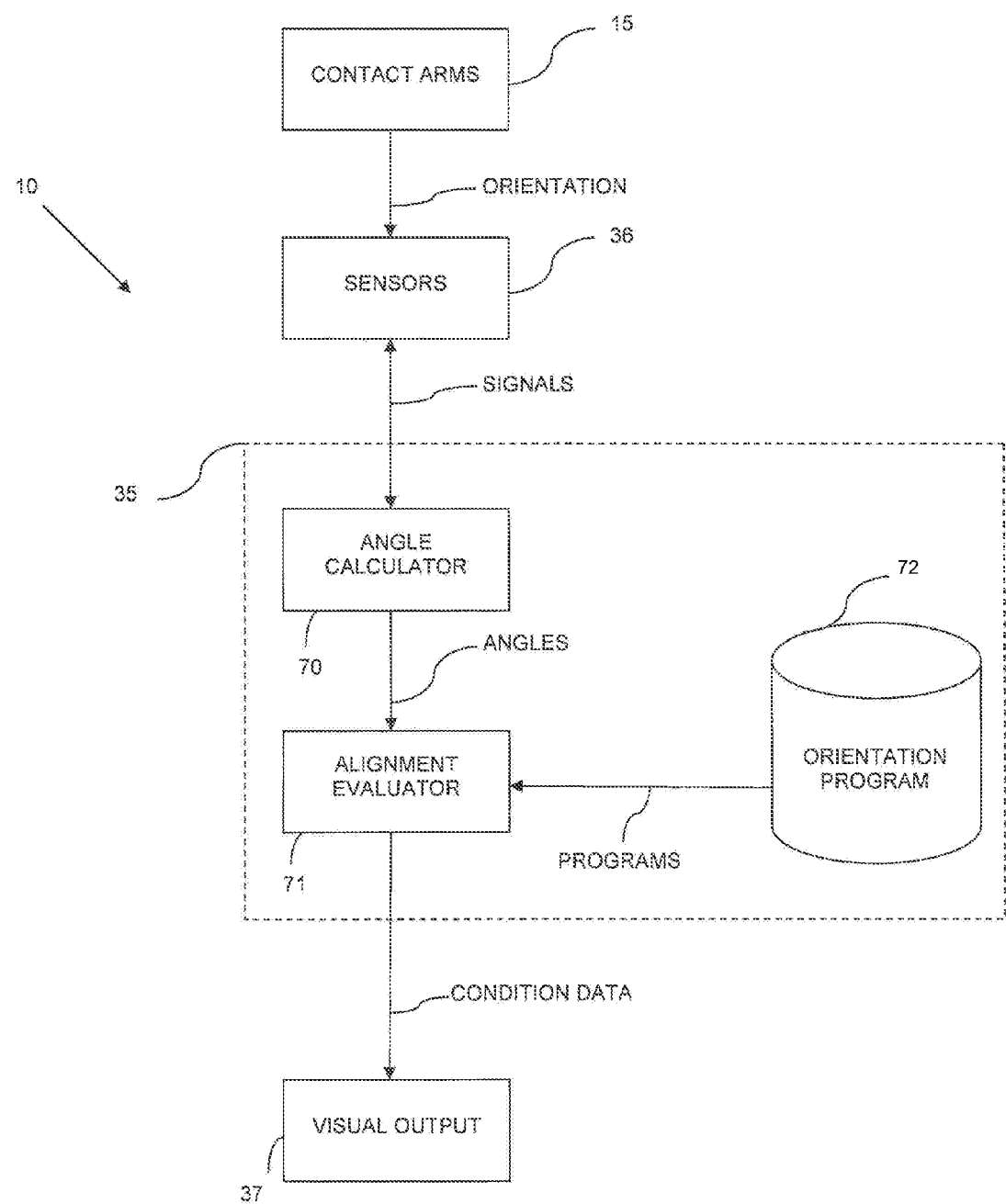
FIG. 7 is a block diagram illustrating components of the hip resurfacing drill guide device of FIG. 1.

Referring to FIG. 7, software components of the guide device 10 are shown in greater detail. As stated above, the contact arms 15 have a variable orientation, and sensors 36 provide a signal indicative of an orientation angle of the contact arms 15 relative to the body 11. The sensors 36 may each be associated with an individual contact arm 15. The PCB 35 comprises an angle calculator 70 that receives the signals from the sensors 36 and will hence determine an orientation angle of each of the contact arms 15 relative to the body 11. An alignment evaluator 71 is responsible for determining whether the device 10 is aligned or misaligned relative to the femur A, e.g., in a "drill" or a "no drill" condition. The alignment evaluator 71 may operate as a function of different orientation programs present in database 72. For instance, based on the embodiment described above, it may be required that diametrically opposed contact arms 15 be at a same orientation (i.e., same angle) relative to the body 11. Alternatively, the orientation program may be patient specific, and hence preoperatively programmed to require that the contact arms 15 each be at a predefined angle, based on patient anatomy. The alignment evaluator 71 produces alignment data that will be seen as visual output by the operator, through the LED units 37.

The device 10 described above, as well as the method associated with the device 10, advantageously sets forth a solution that is non-demanding in terms of pre-operative preparation over prior art systems.

The invention claimed is:
1. A device for guiding a drilling of a femoral head of a femur in femoral head resurfacing comprising:
    a body, the body defining at least one guide channel adapted to receive and guide a drilling component therein, the at least one guide channel having a concentric guide direction;

arms pivotally connected to the body and biased toward one another about pivot axes being transverse to the concentric guide direction, the arms each having a contact end extending below the body, the contact ends adapted to contact a femoral neck when the body is in a hovering position relative to the femoral head;

at least one sensor producing a signal indicative of an orientation angle of each of the arms relative to the body;

a processor unit for calculating the orientation angles of the arms from the signal, and for evaluating from the orientation angles an alignment of the body relative to the femur; and a visual output producing a visual signal representative of said alignment.

2. The device according to claim 1, wherein each of said arms has a straight portion connected to the body by a pivot, a curved portion adapted to be opposite the femoral head in the hovering position of the body, and wherein the contact ends of the arm are at an end of the curved portion.

3. The device according to claim 1, comprising 4, 6 or 8 of the arms.

4. The device according to claim 1, wherein the contact ends of the arms each comprise a curved contact surface.

5. The device according to claim 1, wherein grooves are defined in an outer surface of the body, the arms being each received in one of the grooves, the grooves constraining the movement of the arms to a single rotational degree of freedom of movement relative to the body.

6. The device according to claim 1, wherein the body has an outer shell defining an inner cavity, and an inner body housing fixedly received in the inner cavity of the outer shell.

7. The device according to claim 6, wherein the processor unit and the visual output are mounted onto the inner body housing.

8. The device according to claim 1, further comprising a pin shaft received in an inner cavity of the body, the pin shaft defining the at least one guide channel.

9. The device according to claim 8, wherein the pin shaft is removably received in the body, complementary engagement means being provided between the pin shaft and the body to adjust an orientation of the pin shaft to a plurality of predetermined orientations.

10. The device according to claim 9, wherein the complementary engagement means are spline-like connectors projecting radially from the pin shaft, and complementary seats defined in the body.

11. The device according to claim 9, wherein the pin shaft has a visual marker thereon to assist in orienting the pin shaft in the body.

12. The device according to claim 1, wherein at least one guide channel is at least one of concentric with a longitudinal axis of the body, at an offset angle relative to the longitudinal axis of the body, and parallel and offset from the longitudinal axis of the body.

13. The device according to claim 1, wherein the visual output comprises a LED unit associated with each of the contact arms, the LED unit producing a red light for misalignment and a green light for alignment.

14. The device according to claim 1, wherein the processor unit evaluates the body as correctly aligned when each said arm of diametrically opposed pairs are at a same orientation angle relative to the body.

15. A method for aligning a drill guide device on a femur for subsequent drilling a femoral head with a guide channel in the drill guide device, the guide channel having a concentric guide direction, the method comprising:

positioning a body of the guide device in a hovering position above a femoral head by passing arms of the guide device over the femoral head to a biased grasping engagement with the femoral neck; and displacing the body in the hovering position until each of the arms is at a desired orientation angle transversely to the concentric guide direction of the guide device such that said arms of diametrically opposed pairs are at a same orientation angle relative to the body, based on an output provided by the guide device.

16. The method according to claim 15, wherein positioning the body comprises abutting a bottom of the body against the femoral head.

17. The method according to claim 15, further comprising inserting a pin shaft in an inner cavity of the body at a desired orientation based on a visual alignment of the pin shaft with a landmark of the femur, the pin shaft including the guide channel.

18. The method according to claim 15, further comprising drilling the femoral head using the guide channel when the arms are at the desired orientation angle.

19. The method according to claim 18, wherein drilling the femoral head comprises drilling a guide wire into position in the femoral head.

20. A method for aligning a drill guide device on a femur for subsequent drilling a femoral head with a guide channel in the drill guide device, the guide channel having a concentric guide direction, the method comprising:

positioning a body of the guide device in a hovering position above a femoral head by passing arms of the guide device over the femoral head to a biased grasping engagement with the femoral neck and by abutting a bottom of the body against the femoral head; and displacing the body in the hovering position until each of the arms is at a desired orientation angle transversely to the concentric guide direction of the guide device, based on an output provided by the guide device.

21. The method according to claim 20, further comprising inserting a pin shaft in an inner cavity of the body at a desired orientation based on a visual alignment of the pin shaft with a landmark of the femur, the pin shaft including the guide channel.

22. The method according to claim 20, further comprising drilling the femoral head using the guide channel when the arms are at the desired orientation angle.

23. The method according to claim 22, wherein drilling the femoral head comprises drilling a guide wire into position in the femoral head.

24. A method for aligning a drill guide device on a femur for subsequent drilling a femoral head with a guide channel in the drill guide device, the guide channel having a concentric guide direction, the method comprising:

positioning a body of the guide device in a hovering position above a femoral head by passing arms of the guide device over the femoral head to a biased grasping engagement with the femoral neck, including inserting a pin shaft in an inner cavity of the body at a desired orientation based on a visual alignment of the pin shaft with a landmark of the femur, the pin shaft including the guide channel; and displacing the body in the hovering position until each of the arms is at a desired orientation angle transversely to the concentric guide direction of the guide device, based on an output provided by the guide device.

25. The method according to claim 24, further comprising drilling the femoral head using the guide channel when the arms are at the desired orientation angle.

26. The method according to claim 25, wherein drilling the femoral head comprises drilling a guide wire into position in the femoral head.

* * * * *